United States Patent
Uchida et al.

[11] Patent Number: 6,093,746
[45] Date of Patent: Jul. 25, 2000

[54] THERAPEUTIC AGENTS FOR ASTHMA

[75] Inventors: Yoshiyuki Uchida, Tsukuba; Haruhiko Sueoka, Setagaya-Ku, both of Japan

[73] Assignees: Yoshiyuki Uchida, Tsukuba; Immuno-Bio Japan Co., Ltd., Tokyo, both of Japan

[21] Appl. No.: 09/097,388

[22] Filed: Jun. 16, 1998

[30] Foreign Application Priority Data

Sep. 5, 1997 [JP] Japan .................................. 9-241004

[51] Int. Cl.$^7$ .................................. A01M 37/52
[52] U.S. Cl. .................................. 514/634; 514/826
[58] Field of Search .................................. 514/634, 826

[56] References Cited

U.S. PATENT DOCUMENTS 5,612,375  3/1997  Sueoka .................................. 514/565

Primary Examiner—Theodore J. Criares
Attorney, Agent, or Firm—Birch, Stewart, Kolasch & Birch, LLP

[57] ABSTRACT

An object of the present invention is to provide safe therapeutic agents for asthma inhibiting the delayed type asthmatic reaction in bronchial asthma and having no side effect. The present invention is a therapeutic agents for asthma containing a compound represented by the under chemical formula or a physiologically acceptable base thereof as an effective ingredient, and the drug containing creatine or a physiologically acceptable base thereof as an effective ingredient.

Chemical Formula

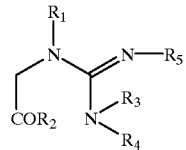

7 Claims, 1 Drawing Sheet

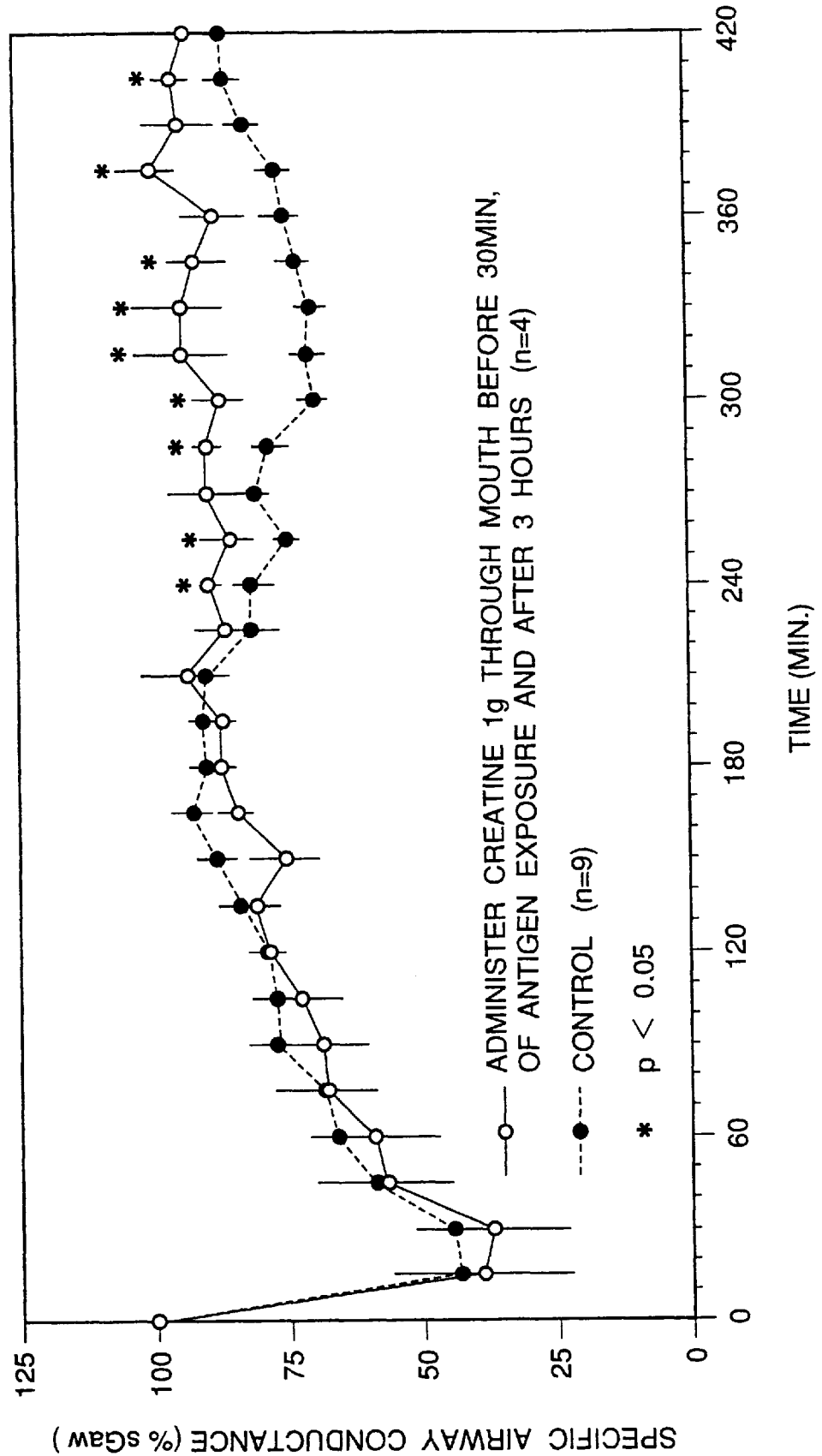

THERAPEUTIC AGENTS FOR ASTHMA

BACKGROUND OF THE INVENTION

1. Field of the Invention

The present invention relates to therapeutic agents for bronchial asthma that effectively suppress asthmatic responses, especially late asthmatic response.

2. Description of the Prior Art

In general, bronchial asthma has been recognized as a disease which is characterized by contraction of smooth muscles in the airway due to type I allergy. However, recent advances in the research of this field have revealed a part of the pathogenesis of asthma, which is characterized by reversal airflow limitation, airway inflammation, mucus hypersecretion and remodeling of the airway structure due to chronic inflammation. Pharmacological therapy should be established beyond understanding of such pathogenesis.

At present available medications for asthma are quick-relievers to reverse airflow limitation such as beta-agonists and xanthine derivatives, and controllers to prevent symptoms by means of suppressing airway inflammation such as corticosteroids inhalants accompanying symptoms like cough, chest tightness and wheezing, while controllers are used daily for a long term basis to suppress persistent inflammation.

However, inhaled corticosteroids as a controller potentiates oropharyngeal candidiasis, dysphonia and occasional coughing from upper-airway irritation in spite that the risk for systemic effects of an inhalant is less than systemic corticosteroids. Moreover, the usage how to inhale steroids is annoying a lot of patients. Long term use of oral or parenteral corticosteroids can cause serious adverse-effects like as osteoporosis, arterial hypertension, diabetes hypothalamic-pituitary-adrenal axis suppression, cataracts, obesity, skin thinning leading to cutancous striae and easy bruisability, and muscle weakness. Controller agents are administered for a long periods, and therefore the systemic side effects of those agents should be avoided or minimized.

From the viewpoint of medical economy, inexpensive asthma-controller medicines have been desired to be developed. Although inhaled corticosteriods are very effective for asthma management, the expensiveness of these drugs has not only a great expense to most of asthmatics but also a burden to national finance of each countries. Nowadays, many patients are probably eager for the development of another type of anti-inflammatory medicines for asthma management instead of inhaled corticosteroids. In such means, a novel and safe anti-asthma medicine has been looked for in this field.

Two kinds of asthmatic responses, i.e., immediate airflow limitation after the antigen challenge and several hours following that, have been recognized to be observed. The early reaction is referred as immediate asthmatic response (IAR) and following phenomenon as late asthmatic response (LAR). IAR has been recognized by airflow limitation which results from acute bronchoconstriction due to allergen exposure, while LAR is due to airway inflammation in the airway. The airway inflammation, which were characterized usually by extensive infiltration of eosinophils, mast cells and mononuclear cells, causes edematous swelling of the airway wall accompanied with or without smooth muscle contraction. Those pathologic changes would be related not only to LAR but also to airway hyperreactivity and aggravating asthma Metzger, W. J. , Hunninghake, G. W. and Richarson, H. B.: Late Asthmatic Responses; Inquiry into Mechanism and Significance, Clin. Rev. Allergy 3:145, 1985). The mechanism of this pathological feature has not been elucidated fully.

SUMMARY OF THE INVENTION

The present invention has been made under the circumstances above, and the object of the invention is to provide a safe drug for treatment of bronchial asthma which has an excellent potency corresponding to that of adrenal cortical hormone, which can inhibit the delayed type asthmatic reaction to particular effect, and which has no side effects.

In such circumstances, the inventors keenly studied to find that the compound represented by the below chemical formula 1 very effectively inhibits asthmatic reactions in bronchial asthma, particularly the delayed type asthmatic reaction, and completed the present invention. Specifically, the present invention is therapeutic agents for asthma containing a compound represented by the chemical formula 1 or a physiologically acceptable base thereof as an effective ingredient, wherein $R_1$ is a hydrogen atom, an alkyl group of which carbon number is "1–6", an aryl group, an aromatic heterocyclic group and a cycloalkyl group of which ring member is "5–7", $R_2$ is a hydroxyl group, a halogen atom, an amino group and an ester group, $R_3$ and $R_4$ are independently hydrogen, an alkyl group of which carbon number is "1–6", an aryl group, a cycloalkyl group of which ring member is "5–7", an aromatic heterocyclic group and a phosphate group, and $R_5$ is hydrogen, an alkyl group of which carbon number is "1–6" and an aryl group.

Chemical Formula 1

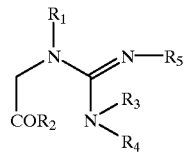

Therapeutic agents for asthma in the present invention means a drug used for so-called treatment performed in the hope of remitting the symptoms of asthma, and preventive treatment. It is known that creatine, a typical compound used in the present invention, is deeply involved with ATP (adenosine triphosphate) which is a kinetic energy. (See, e.g., Roger Hariss, Eric Hultman, Clinical Science (1993): 84, 565–5711.) However, no effect of such compounds as creatine for asthma has been known yet. The chemical formula of creatine is as shown in the chemical formula 2 below.

Chemical Formula 2

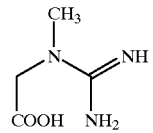

BRIEF DESCRIPTION OF THE DRAWING

FIGURE is a graph showing the asthmatic reaction inhibitory effect of creatine in antigen induced asthmatic guinea pigs.

DESCRIPTION OF THE PREFERRED EMBODIMENTS

The compound used as an effective ingredient of the therapeutic agents for asthma of the invention is represented by the chemical formula 1 above (hereafter referred to as "compound A") wherein, within $R_1$, the alkyl group of which carbon number is "1–6" includes, for example, a methyl group, an ethyl group, a propyl group, an isopropyl group, an n-butyl group, an isobutyl group, a sec-butyl group and a pentyl group. The aryl group includes, for example, a phenyl group, and the cycloalkyl group includes, for example, a cyclopentyl group, a cyclohexyl group and cycloheptyl group. The aromatic heterocyclic group includes, for example, a pyridyl group, a pyrimidyl group, an imidazolyl group, an oxazolyl group, an iso-oxazolyl group, a thiazolyl group and a furyl group. The aromatic heterocyclic group may have one or more substituents including, for example, an alkyl group of which carbon number is "1–6" or an alkoxyl group of which carbon number is "1–6", a halogen atom, a carboxyl group and a hydroxyl group. Within $R_2$, the amino group includes, for example, a methylamino group, an ethylamino group, diethylamino group and propylamino group. The ethyl group of $R_2$ includes, for example, a methyl group, an ethyl group, a propyl group, an isopropyl group and an n-butyl group. Within $R_3$, $R_4$ and $R_5$, the alkyl group of which carbon number is "1–6" includes, for example, a methyl group, an ethyl group, a propyl group, an isopropyl group, an n-butyl group, an isobutyl group, a sec-butyl group and a pentyl group. The aryl group includes, for example, a phenyl group, and the cycloalkyl group includes, for example, a cyclopentyl group and cycloheptyl group. The aromatic heterocyclic group includes, for example, a pyridyl group, a pyrimidyl group, an imidazolyl group, an oxazolyl group, an isooxazolyl group, a thiazolyl group and a furyl group.

The phosphate group of $R_3$ and $R_4$ includes, for example, metaphosphate, pyrophosphate and holtphosphate.

A typical compound of compound 1 is creatine represented by the chemical formula 2, which may alternatively be a compound that is thought to be a derivative of creatine whose concrete example is shown below.

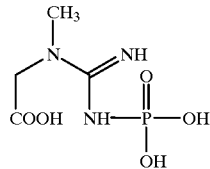

Chemical Formula 3

Also a physiologically acceptable base derived from these compounds may be used in the present invention.

The compound A itself is a known substance which can be made according to, for example, a method described in "Merck Index" page 2566, or a method described in U.S. Pat. No. 5,612,375. The therapeutic agents for asthma of the present invention can be made by adding additive agents such as a lubricant, a disintegrating agent, a binder and excipients to the compound A or physiologically acceptable base thereof and following a commonly known method, and the therapeutic agents can be formed into a formulated product for oral or parenteral administration such as a tablet, a capsule, powder, a fine granule, liquid, suspension, emulsion, a dry syrup, an inhalant, an injection, a suppository.

It was found that the compound A or physiologically acceptable base thereof has an excellent inhibitory effect against the delayed type asthmatic reaction in bronchial asthma as shown in the example test described below. With regard to its side effects, it has been reported in Clinical Science 1992, No. 20, P367–374 that clinical success was made of one-year administration of 1.5 g of the compound to patients with choroidal and retinal atrophy, and that serious side effect was observed when taken by athletes.

Although the dose of the compound 1 or physiologically acceptable base thereof varies with routes of administration, symptoms or weight of a patient and so on, it is generally preferable to administer 1000 mg to 10000 mg per day, and particularly preferable to administer 2000 mg to 6000 mg per day to an adult orally.

The present invention is further illustrated by the following example, which does not limit the invention.

EXAMPLE TEST-1

The pulmonary function was detected and observed under a non-anesthetic condition with spontaneous respiration to confirm the effect of creatine to antigen induced asthmatic guinea pigs.

Methods (1) Animal (Object)

A Hartley female guinea pig (SLC) (about 350 g of weight) was sensitized by intra-peritoneal injection of 30 mg/kg of cyclophosphamide and, two days after that, intra-peritoneal injection of 1 mg of ovalbumin (OA) and 100 mg of alumina, and the animal was further subjected to booster sensitization by, after three weeks, intra-peritoneal injection of 0.001 mg of OA and 100 mg of alumina.

(2) Apparatus and Appliance

Pressure type body plethysmograph

Pneumotachograph ("TV-241T", Nihon Koden Corp in Japan.)

Differential transducer ("T-601", Nihon Koden Corp in Japan.)

Airflow resistance tube (Lilly type, Nihon Koden Corp in Japan.)

Oscilloscope ("DS-9121", Iwatsu Electric Co., Ltd in Japan.)

Computer ("Macintosh Centris 660AV", Apple Computer in U.S.A.)

Software (respiration analysis software created by Lab View for Macintosh 3.01)

Nebulizer ("NE-U11", Omron Corp in Japan)

(3) Methods for Administration of the Drug and Exposure to Antigen

Creatine pretreatment group 100 mg of creatine was suspended with 1 ml of a weak alkaline buffer, and was administered into the esophagus using an esophageal catheter 30 minutes before and 3 hours after exposure to the antigen. The weak alkaline buffer was constituted with 1 ml of distilled water, 0.5 mg of sodium carbonate and 0.2 mg of citric acid.

Control group 1 ml of the alkaline buffer was administered into the esophagus using an esophageal catheter 30 minutes before exposure to the antigen.

Method for exposure to antigen 40 mg of OA was dissolved in 10 ml of physiological saline (4 mg/ml) and was inhaled using an ultrasonic nebulizer for 2 minutes.

(4) Method for Detecting Pulmonary Function

Guinea pigs were mounted on a pressure type body plethysmograph, and rates of change of specific conductance of airway (sGaw) were detected according to the method of Agrawal (Aglawal, K. P.; Specific airway conductance in guinea pigs: Normal values and histamine induced fall. Respiratory Physiology 43:23, 1981). Changes of airflow from the noses and internal pressure of the box were monitored, wave forms of the air flow and the pressure were digitally sampled at 1024 Hz, dots from the end of respiration over to the beginning of respiration were regressed, and sGaw was detected from the slope (tan) of the regression line. The sGaw was determined before exposure to antigen, then physiological saline was inhaled for 2 minutes to confirm that there was no change in sGaw, and it was confirmed, using this value as 100%, that there was no change in sGaw after exposure to antigen, and the rates of change after exposure to antigen were observed using this value as 100%.

Results

FIGURE shows the results. The sGaw after exposure to antigen was detected by measuring sGaw every 15 minute for 7 hours. The sGaw at each time was compared between the administration group and the no administration group. A statistical study was performed using Student's t-test. According to the t-test, P<0.05 was determined to be significant. In the no creatine group, airway obstruction occurred from immediately after exposure to antigen (immediate type asthmatic reaction), sGaw was restored to the previous value after about 2 hours, and airway obstruction was observed again from after 3 hours (delayed type asthmatic reaction). In the creatine group, the delayed type asthmatic reaction was inhibited with statistical significance. As evident form this, creatine has an excellent effect against the delayed type asthmatic reaction.

EXAMPLE TEST-2

Seven asthmatics (average age; 40, 4 males and 3 females) took 4 g/day creatine orally, and all of showed improvement of pulmonary function and decreased in frequency of on-demand uses of $\beta_2$-stimulant-inhalants.

All patients use inhaled steroids over 800 µg/day and are categorized into step 1 or $2^1$. Pulmonary function parameters, e.g., mean (SD) of PEF,309(83), mean (SD) of FEV1(L);2.12(0.64) changed into 361(79) and 2.38(0.57) in 1 month after the creatine suplementation, respectively. While, frequency of uses of $\beta_2$-stimulant decreased from 3.2-times dairy uses to 0.3-times. Those improvements showed statistically significant (p<0.01). Every patient showed improvement of pulmonary function within 1 month. In general, it seems to take at least one month to saturate creatine in skelton muscles, and an effective delay showing improvement is understandable.

Since creatine has been safely used as one of sports supplements, its application for asthmatics would not bring any problems. Those indicate that creatine is not only an enhancer in skelton muscles but also an agent of anti-inflammation.

Thus, the drug of the present invention has an excellent inhibitory effect against the delayed type asthmatic reaction in bronchial asthma. Also the drug of the present invention has no side effect and is safe for the human body.

It should be understand that many modifications and adaptations of the invention will become apparent to those skilled in the art and it is intended to encompass such obvious modifications and changes in the scope of the claims appended hereto.

What is claimed is:

1. A method of treating asthma comprising administering creatine to a patient in need thereof.

2. A method for the treatment of bronchial asthma which comprises administering to a patient in need thereof a therapeutic agent for treating asthma containing a compound represented by the following general formula or a physiologically acceptable base thereof as an effective ingredient,

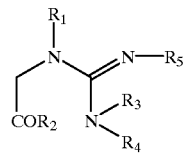

wherein $R_1$ is a hydrogen atom, an alkyl group of which carbon number is 1–6, an aryl group, an aromatic heterocyclic group or a cycloalkyl group of which ring member is 5–7, $R_2$ is a hydroxyl group, a halogen atom, an amino group or an ester group, $R_3$ and $R_4$ are independently hydrogen atom, an alkyl group of which carbon number is 1–6, an aryl group, a cycloalkyl group of which ring member 5–7, an aromatic heterocyclic group or a phosphate group, and $R_5$ is hydrogen atom, and alkyl group of which carbon number is 1–6 or an aryl group.

3. The method of claim 2, wherein the therapeutic agent for treating asthma comprises creatine or a physiologically acceptable base thereof as an effective ingredient.

4. The method of claim 2, wherein the therapeutic agent for treating asthma is a drug for treatment of bronchial asthma.

5. The method of claim 2, wherein the therapeutic agent for treating asthma is an inhibitor of the delayed type asthmatic reaction of bronchial asthma.

6. The method of claim 2, wherein said therapeutic agent is administered in a dose of 1,000 mg to 10,000 mg per day.

7. The method of claim 2, wherein said therapeutic agent is administered in a dose of 2,000 mg to 6,000 mg per day to an adult orally.

* * * * *